US011890435B2

United States Patent
Takagi

(10) Patent No.: US 11,890,435 B2
(45) Date of Patent: Feb. 6, 2024

(54) METHOD AND APPARATUS FOR MINIMIZING EXCESS DRUG DELIVERY

(71) Applicant: Terumo Corporation, Tokyo (JP)

(72) Inventor: Ayu Takagi, Tokyo (JP)

(73) Assignee: Terumo Corporation, Tokyo (JP)

( * ) Notice: Subject to any disclaimer, the term of this patent is extended or adjusted under 35 U.S.C. 154(b) by 357 days.

(21) Appl. No.: 17/127,763

(22) Filed: Dec. 18, 2020

(65) Prior Publication Data

US 2021/0187256 A1 Jun. 24, 2021

Related U.S. Application Data

(60) Provisional application No. 62/950,039, filed on Dec. 18, 2019.

(51) Int. Cl.
*A61M 25/10* (2013.01)

(52) U.S. Cl.
CPC .. *A61M 25/10184* (2013.11); *A61M 25/1025* (2013.01); *A61M 2025/105* (2013.01); *A61M 2025/1052* (2013.01); *A61M 2025/1056* (2013.01)

(58) Field of Classification Search
CPC .... A61M 2025/1015; A61M 2025/105; A61M 2025/1052; A61M 2025/1056; A61M 25/10184; A61M 25/104
See application file for complete search history.

(56) References Cited

U.S. PATENT DOCUMENTS

| | | | |
|---|---|---|---|
| 6,921,411 B2 | 7/2005 | Yock | |
| 2003/0233065 A1 | 12/2003 | Steward et al. | |
| 2006/0135985 A1* | 6/2006 | Cox | A61M 25/1002 606/194 |
| 2011/0218494 A1 | 9/2011 | Gerrans et al. | |
| 2014/0142598 A1 | 5/2014 | Fulton, III | |
| 2015/0313732 A1* | 11/2015 | Fulton, III | A61F 2/82 623/1.11 |
| 2017/0258613 A1 | 9/2017 | Franano et al. | |
| 2018/0206862 A1 | 7/2018 | Long | |

OTHER PUBLICATIONS

WIPO, U.S. International Search Authority, International Search Report and Written Opinion dated Mar. 17, 2021 in International Patent Application No. PCT/US2020/066219, 8 pages.
European Patent Office, Extended European Search Report dated Dec. 1, 2023 in European Patent Application No. 20902219.3, 8 pages.

* cited by examiner

*Primary Examiner* — Deanna K Hall
(74) *Attorney, Agent, or Firm* — Inskeep IP Group, Inc.

(57) ABSTRACT

A device and method are described for aspirating within a patient during the delivery of a drug-coated treatment device to help remove drug coating dislodged in a patient's blood. The drug treatment device can be a drug-coated balloon, a drug-coated stent, or similar devices. The device can include an occlusion balloon to help contain the dislodged drug coating and aspiration can be applied proximally, distally, or both proximally and distally of the drug coated balloon during a procedure.

19 Claims, 6 Drawing Sheets

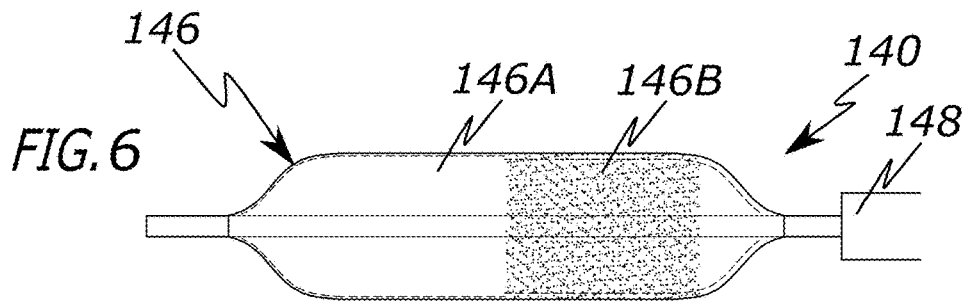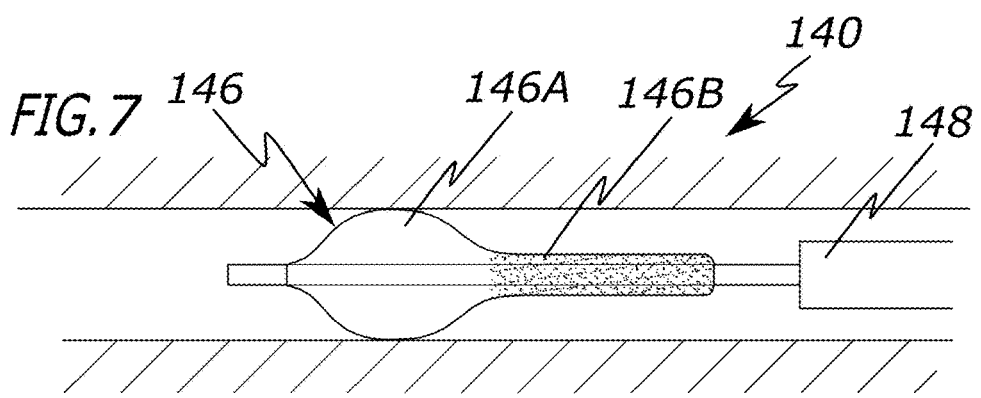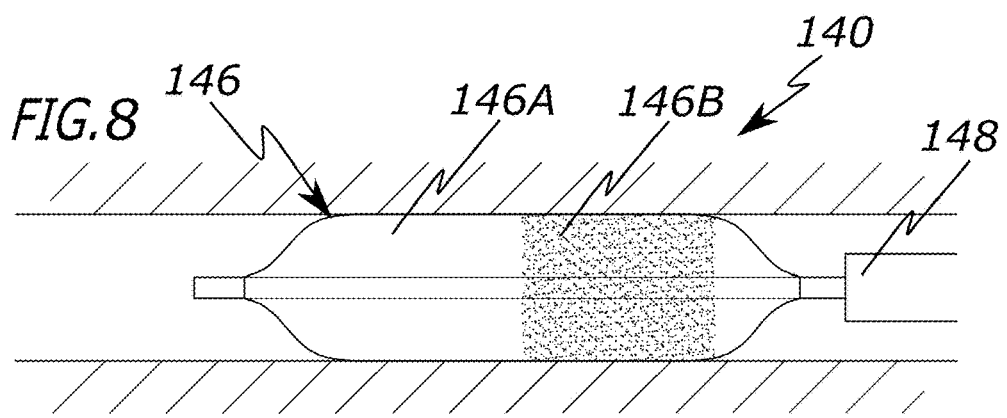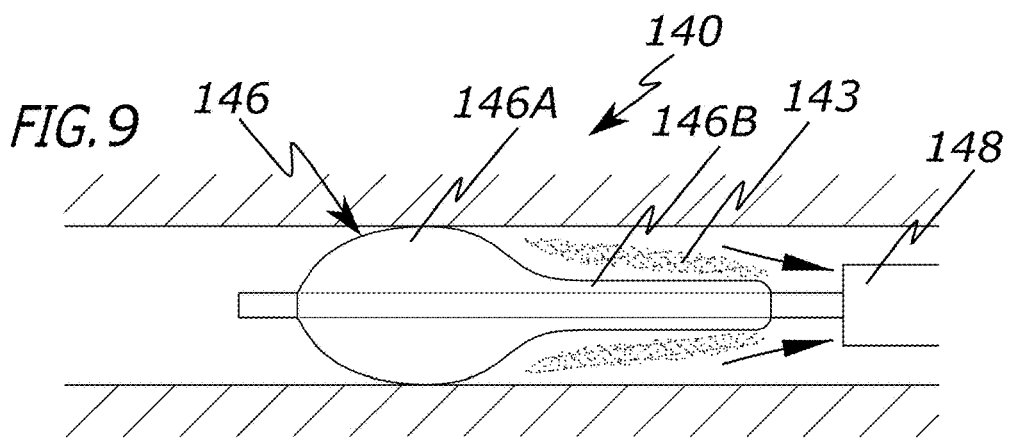

METHOD AND APPARATUS FOR MINIMIZING EXCESS DRUG DELIVERY

RELATED APPLICATIONS

This application claims benefit of and priority to U.S. Provisional Application Ser. No. 62/950,039 filed Dec. 18, 2019 entitled Minimizing Drug Deposits During Drug Delivery Procedures, which is hereby incorporated herein by reference in its entirety.

BACKGROUND OF THE INVENTION

A variety of vascular procedures utilize drug-coated devices to impart a drug or similar substance to a specific portion of tissue within a patient. These drugs are often used to treat or prevent stenosis, restenosis, sclerosis, or similar vessel diseases.

In one specific example, a balloon catheter can be used for such drug delivery purposes. The catheter's balloon includes a drug coating on its outer surface that, when expanded, presses the drug coating against an inner surface of the vessel so that at least some of the drug coating is imparted to the contacted tissue. In another example, a stent can include a drug coating on its surfaces that is imparted to the vascular tissue that the stent expands against, allowing the drug to be absorbed by the tissue.

While drug coatings on such devices remain an important method of drug delivery to targeted areas of the vasculature, a significant portion of the drug coating can be dislodged or freed during the delivery procedure. Once free, the drug can migrate within the blood and vasculature of the patient to numerous unintended locations and can thereby cause undesirable complications to the patient.

For example, paclitaxel is sometimes incorporated into a drug coating on a balloon catheter for treatment of restenosis or vessel narrowing. Paclitaxel is particularly desirable for application via a balloon catheter due to its high concentration and rapid release from the coating. However, the paclitaxel treatment via both balloons and stents has also been associated with an increased risk of death. One possible cause of this mortality increase is the release of paclitaxel into the patient's blood stream where it can travel to organs that are particularly sensitive to the drug, such as the lungs. In treatment instances with relatively higher concentrations of paclitaxel in the drug coating, measurable concentrations of paclitaxel in the patient's blood may remain for 30 days or longer.

The unintended release of drugs from a drug coating is further complicated by the nature of the coating itself. If the coating is too resistant to being removed from the device, very little of the drug will be released to the patient's tissue. If the coating is too easily removed, large portions of the drug may end up circulating in the patient's vascular system. Hence, delivering a desired amount of drug with such coatings will often necessitate the release of some or even a substantial portion of the drug into the bloodstream.

Indeed, the Applicants have performed experiments and analyses and determined the following statistics: less than 1% of a drug is transferred to a target tissue area from a typical balloon coating while only about 16% of the coating remains on the balloon after the procedure is complete. About 25% of the drug coating is removed while tracking the balloon catheter through a guide catheter and about 59% of the drug coating is removed during balloon inflation, deflation, and removal from the catheter. As a result, about 84% of the drug coating is removed from the balloon during a procedure and is believed to be distributed throughout the patient's vascular system and organs. Depending on the type of drug coating, the concentration of the drug in the coating, and the type of balloon (or other device), a significant amount of the drug can often be measured in a patient's blood for a period of time after treatment.

For at least these reasons, there is a need for improved treatment methods and devices that reduce the amount of drugs unintentionally released into a patient's bloodstream during treatment.

SUMMARY OF THE INVENTION

At least one embodiment is directed to a device for aspirating within a patient during the delivery of a drug-coated treatment device to help remove drug coating dislodged in a patient's blood. The drug treatment device can be a drug-coated balloon, a drug-coated stent, or similar devices.

At least one embodiment is directed to a treatment system and method of use that creates aspiration near a distal portion of a drug-coated treatment device, near a proximal portion of a drug-coated treatment device, or aspiration at a combination of both locations. Aspiration can occur while distally advancing a delivery device within a patient's vascular system, while radially expanding/implanting a drug-coated treatment device, while proximally withdrawing a drug-coated treatment device, and/or at any points in between or near in time.

At least one embodiment is directed to a method and treatment system having a balloon catheter having a proximal drug-coated balloon configured to expand against a vessel and a distal occlusion balloon configured to occlude a vessel. The treatment system may further include a guide catheter (or alternately a guiding sheath or introducer sheath) configured to aspirate material from its distal end during a procedure.

At least one embodiment is directed to a method and treatment system having a balloon catheter with a balloon that sequentially inflates. The balloon has a distal portion that inflates first and is generally free of drug-coating. The balloon also has a proximal portion that inflates second and includes a drug coating. The treatment system may further include a guide catheter (or alternately a guiding sheath or introducer sheath) configured to aspirate material from its distal end during a procedure.

At least one embodiment is directed to a method and treatment system having a balloon catheter with a drug-coated balloon and a guidewire lumen configured to aspirate from a distal end of the balloon catheter. The guidewire lumen may have a relatively larger diameter and can be connected to an aspiration source. The balloon catheter may optionally be used with a proximally placed occlusion balloon and/or a guide catheter (or alternately a guiding sheath or introducer sheath) configured to also provide aspiration.

At least one embodiment is directed to a method and treatment system having a balloon catheter with an aspiration passage that extends through a drug-coated balloon and that can be selectively connected to a guide catheter (or alternately a guiding sheath or introducer sheath) to create aspiration therethrough. The guide catheter can be configured to provide aspiration and its distal end connectable to the passage of aspiration passage, allowing aspiration distally of the drug-coated balloon. Optionally, an occlusion balloon can be advanced through the aspiration passage and used distally of the drug-coated balloon.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 6 is a side view of the sequentially inflatable balloon catheter of FIG. 5.

FIG. 7 is a side view of the sequentially inflatable balloon catheter of FIG. 5.

FIG. 8 is a side view of the sequentially inflatable balloon catheter of FIG. 5.

FIG. 9 is a side view of the sequentially inflatable balloon catheter of FIG. 5.

DESCRIPTION OF EMBODIMENTS

Figure 1:
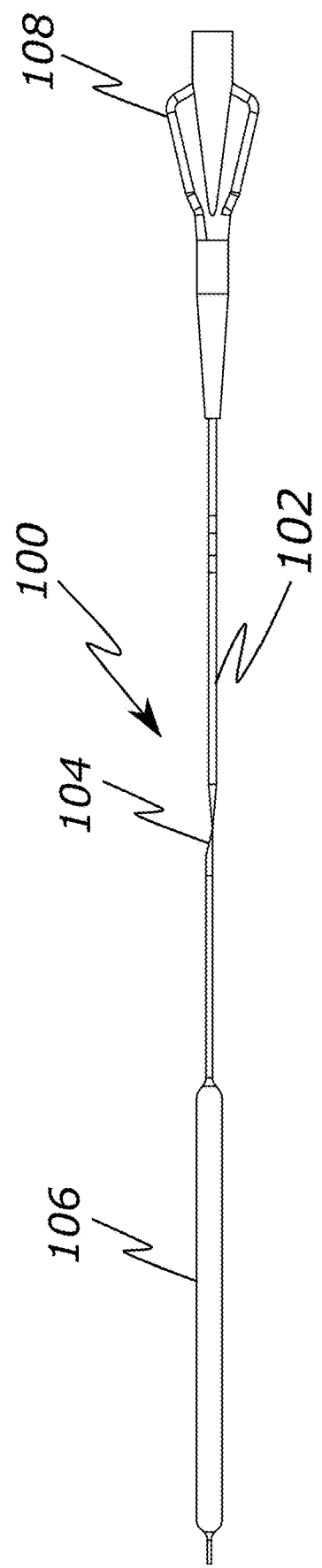
FIG. 1 is a side view of a balloon catheter.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements. While different embodiments are described, features of each embodiment can be used interchangeably with other described embodiments. In other words, any of the features of each of the embodiments can be mixed and matched with each other, and embodiments should not necessarily be rigidly interpreted to only include the features shown or described.

While the terms drug and drug coating are used in this specification, it is intended that these terms are inclusive of any therapeutic agents, compounds, chemicals, or other materials that can be incorporated into a coating on a device.

As previously discussed, drug coated devices such as balloon catheters and stents often release an undesirable amount of their drug coating into the blood during treatment procedures which then circulates through the vascular system of the patient. Much of this unwanted drug release may occur when the device (e.g., balloon or stent) is being tracked through an outer guide catheter, during expansion of the device within the patient's vessel, during contraction of the device, and during retraction back into the guide catheter.

Figure 2:
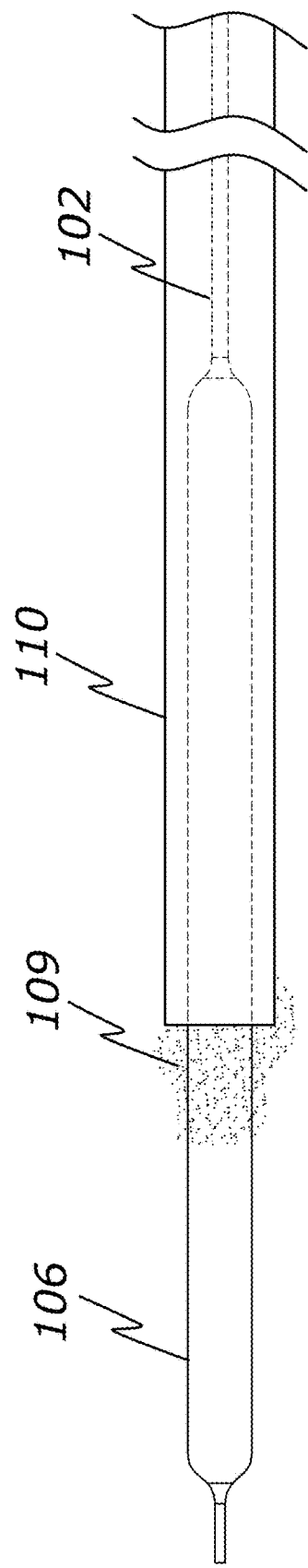
FIG. 2 is a side view of a balloon catheter within a guide catheter.

One specific example of such undesirable loss of drug coating can be seen in FIGS. 1 and 2. FIG. 1 illustrates a typical balloon catheter 100 having a drug coated balloon 106 located at the distal end of an elongated catheter body 102. The catheter body 102 also includes a guidewire passage 104 opening proximally and distally of the balloon 106, as well as a balloon inflation lumen (not shown) that communicates between the interior of the balloon 106 and a proximal catheter hub 108 to allow balloon inflation. While this guidewire passage 104 configuration is typically referred to as a rapid exchange catheter style, over-the-wire style catheters which include a guidewire passage opening at the proximal end of the catheter is also contemplated.

Referring to FIG. 2, the balloon catheter 100 is typically advanced out of an overlying guide catheter 110 so that the drug coated balloon 106 is positioned adjacent to the vessels wall of a target treatment area. Inflation media is injected into the inflation lumen causing the drug coated balloon 106 to inflate and contact the wall of the vessel where at least some of the drug coating is delivered to the vessel wall. Finally, the drug coated balloon 106 is deflated and retracted back into the overlying guide catheter 110. Note that while a guide catheter is used throughout this specification, it should be understood a guiding sheath or introducer sheath can alternately be used as this component, throughout this specification.

As seen in FIG. 2, much of the drug coating 109 becomes free from the balloon 106 during this treatment procedure where it mixes with the patient's blood and circulates through at least a portion of the patient's vascular system and organs, such as the heart and lungs. Depending on the type of drug, the amount freed from the balloon, the treatment location, and other factors, a significant and undesirable concentration of the drug can remain in the patient's blood and/or organs for days or even weeks after a treatment procedure.

The present specification describes several treatment devices and methods for reducing the unwanted accumulation of drugs dislodged from the coating of a treatment device. While different embodiments of balloon catheters are primarily described, it should be understood that the present devices and methods can be similarly adapted for used with other drug coated devices, such as stents, or even non-coated devices that directly deliver drugs to a target area (e.g., a weeping balloon configured to excrete drugs from its pores).

Figure 3:
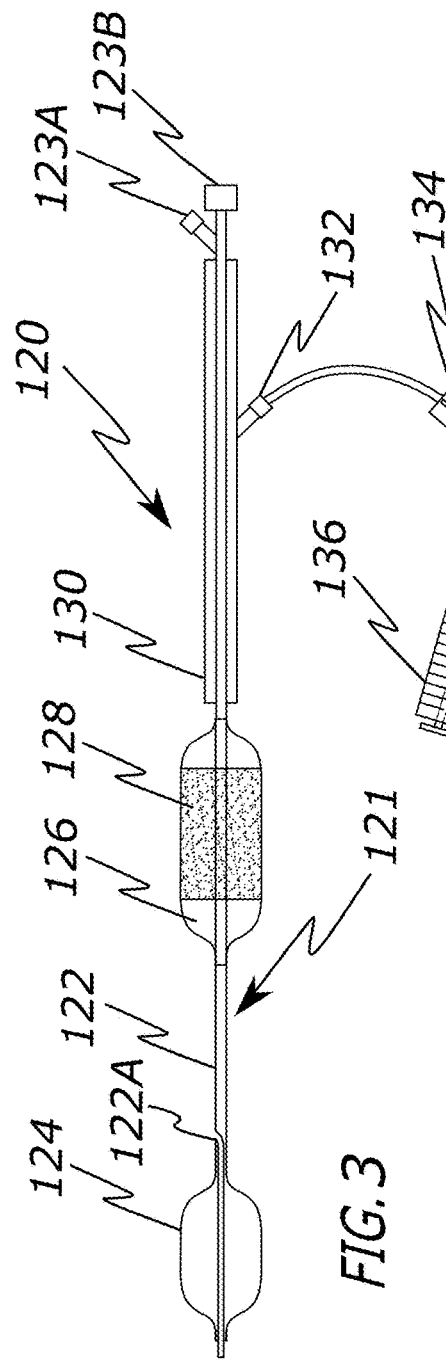
FIG. 3 is a side view of a dual balloon catheter within a guide catheter.
Figure 4:
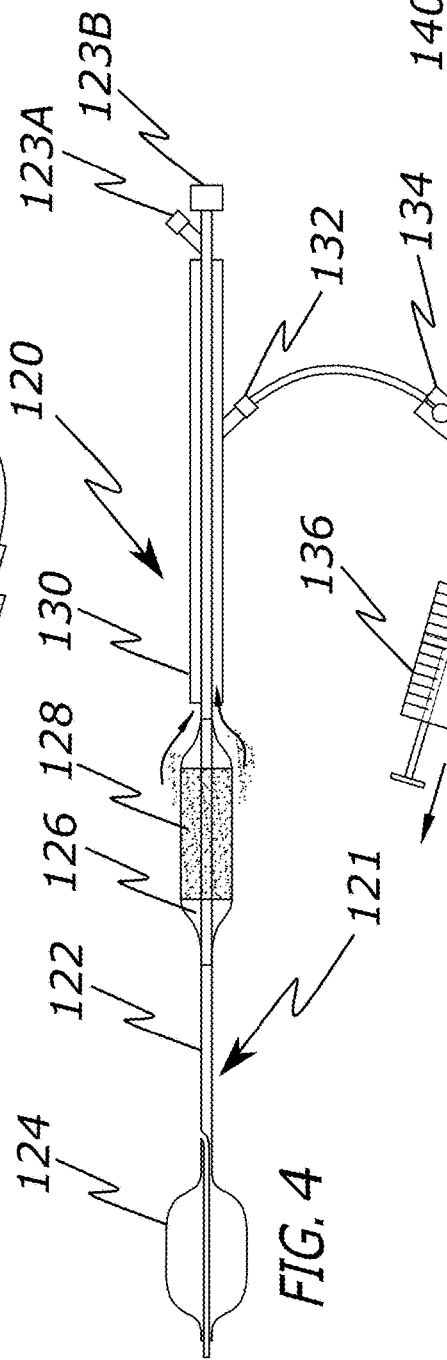
FIG. 4 is a side view of the dual balloon catheter of FIG. 3.

FIGS. 3 and 4 illustrate one embodiment of a treatment system 120 configured to aspirate or remove at least some of the drug coating released into a patient's vascular system during a treatment procedure. The treatment system 120 includes a balloon catheter 121 having an occlusion balloon 124 configured to occlude a distal portion of the patient's target vessel prior to inflation of a drug-coated balloon 126. As discussed in detail below, blood containing any free or released drug coating during the procedure is aspirated and removed from the patient to prevent circulation through the patient's vessels.

The occlusion balloon 124 is located distally of the drug-coated balloon 126 on an elongated body 122 of the balloon catheter 121. The balloons 124 and 126, as well as the elongated body 122, are configured to allow the occlusion balloon 124 to fully inflate prior to significant inflation of the drug-coated balloon 126 and to allow the occlusion balloon 124 to deflate after deflation of the drug-coated balloon 126. This inflation sequence helps keep the vessel occluded during portions of the procedure in which the drug coating is most likely to dislodge into the patient's blood—as such the occlusion balloon 124 helps prevent distal migration of drug from drug-coated balloon 126 and/or, as will be explained in more detail, helps provide a seal for a subsequent aspiration procedure. In one example, this inflation sequence can be achieved with two separate inflation lumens within the elongated body 122, each of which are connected to a separate inflation lumen and inflation ports (e.g., ports 123A and 123B) at the proximal end of the elongated body 122.

In another example, both balloons 124, 126 may be connected to a single inflation lumen in the body 122. To create the desired inflation sequence, the occlusion balloon 124 may be composed of a material that is easier to inflate than the drug-coated balloon 126. In one specific example, the occlusion balloon 124 may be composed of a relatively non-elastic material which increases in diameter with little resistance (e.g., similar to inflating a plastic bag) while the drug-coated balloon 126 may be composed of a relatively elastic material that stretches during inflation to thereby provide resistance (e.g., similar to a rubber party balloon). Hence, as the pressure in the inflation lumen rises, the occlusion balloon 124 inflates first, the drug-coated balloon 126 inflates second, the drug coated balloon 126 deflates first, and the occlusion balloon 126 deflates last.

In either of the previously described balloon inflation examples, the proximal end of the elongated body 122 (e.g., catheter hub) may be connected to one or more manually actuated syringes to cause inflation or to a motorized inflation device. In the case of a motorized inflation device, it may be desirable to provide and hold various pressure levels within the inflation lumen and balloons, particularly with the example of the previously described single inflation lumen since those different levels of pressure within the inflation lumen determine the sequence of inflation of the two balloons 124, 126 (e.g., a low pressure may only inflate occlusion balloon 124 and a higher pressure also inflates the drug-coated balloon 126). In that regard, the motorized inflation device may include algorithms configured to provide a predetermined sequence of pressure levels to achieve a desired balloon inflation and deflation order.

As previously discussed, the treatment system 120 is also configured to provide aspiration to remove any blood near the drug-coated balloon containing any of the drug coating 128 that has been dislodged. In the present embodiment, this aspiration can be provided via an outer guide catheter 130 or sheath in which the balloon catheter 121 is positioned through. The guide catheter 130 may have a generally tubular body and may include an aspiration port 132 that opens to the interior lumen of the guide catheter 130, allowing a vacuum source, such as a syringe 136 or a pump, to be connected to it. When the vacuum source is activated, it causes blood from a distal end of the guide catheter 130 to be pulled into its lumen and towards the vacuum source. Since guide catheters typically include hemostatic valves on their proximal ends (e.g., surrounding the balloon catheter 121), air is prevented from being pulled into the lumen of the guide catheter 130. In other words, the guide catheter 130 is configured only to allow aspiration from its distal end towards the vacuum source and not from the proximal end of the guide catheter 130. In the present embodiment, the continued occlusion of the vessel helps prevent the dislodged drug particles from migrating through the patient's vascular system before the guide catheter 130 can aspirate these drug particles out of the patient.

In the case of using a syringe 136 as the vacuum source, a physician may initially maintain a stopcock valve 134 located between the syringe 136 and guide catheter 130 in a closed position. The plunger of the syringe 136 can be withdrawn to create a vacuum pressure, and then the stopcock valve 134 can be opened when aspiration within the patient is desired. Blood from areas near the drug-coated catheter 126 is then pulled into the guide catheter 130 and further into the syringe 136. Different amounts of blood may be aspirated based on the location of the procedure, the nature of the drug coating, and other factors. A 30 cc or 60 cc syringe or aspiration volume may be appropriate in many instances.

The treatment system 120 can be used, in one example, by first advancing a guidewire into a patient's vascular system so that its distal end is located near a desired treatment location within vessel. Next, the guide catheter 130 can be advanced over the guidewire so that its distal end is located near the desired treatment location. The balloon catheter 121 is then advanced over the guidewire via its guidewire passage 122A so that the drug-coated catheter 126 is positioned at the desired target location and the occlusion balloon 124 is positioned distally of the target location. Optionally, the guidewire can be retracted prior to inflation of the balloons 124, 126.

Next, the occlusion balloon 124 is inflated so that it occludes the vessel and substantially prevents blood from flowing past it. Once the vessel is occluded, the drug-coated balloon 126 is inflated such that the drug coating 128 on the balloon 126 contacts the inner surface of the vessel, delivering or imparting its drug coating to the vessel's tissue, as seen in FIG. 3.

As previously discussed, the processes of tracking the balloon catheter 121 through the guide catheter 130, inflating the drug-coated balloon 126, deflating the drug-coated balloon 126, and other movements during the procedure can dislodge or free a substantial portion of the drug coating 128. In that respect, as the drug-coated balloon 126 is deflated (either partially or fully), the physician can apply aspiration through the guide catheter 130. However, aspiration may also be applied throughout the tracking and inflating processes as well. Again, this aspiration may be generated by opening a valve 134 connected to a syringe 136 with a retracted plunger, among other techniques.

As seen in FIG. 4, the blood and dislodged drug coating 128 are pulled into the guide catheter 130, out port 132, and into the syringe 136 (though some blood and coating may also remain in the guide catheter 130). In one example, the physician may remove 30 to 60 milliliters of blood from the area between the occlusion balloon 125 and the distal end of the guide catheter 130. Finally, the drug coated balloon 126 is completely deflated (if not already fully deflated) and the occlusion balloon 124 is also fully deflated, allowing the physician to proximally withdraw the balloon catheter 121 back into the guide catheter 130 so that the procedure can be completed. Hence, much of the dislodged drug coating that would otherwise circulate through the patient's vascular system is removed from the patient.

FIGS. 5-10 illustrate another embodiment of a balloon catheter 140 with a single, sequentially inflatable balloon 146 that can first partially inflate to occlude a portion of the patient's vessel and then fully inflate to deliver therapeutic agents to the vessel's tissue. Similar to the previously described balloon catheter 121, this allows a portion of the patient's vessel to be occluded to prevent dislodged drug migration and then aspirated to remove any of the dislodged drugs within the patient's blood.

Figure 5:
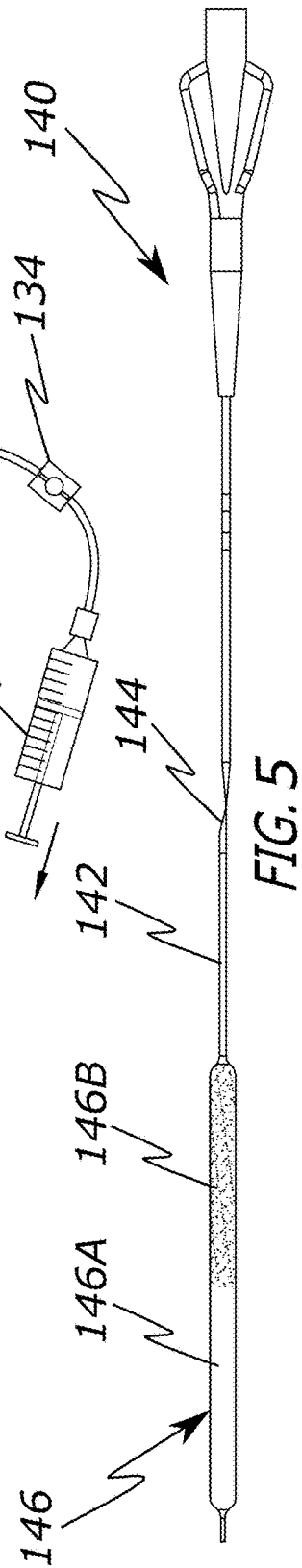
FIG. 5 is a side view of a sequentially inflatable balloon catheter.

As seen in FIGS. 5 and 6, the balloon catheter 140 includes an elongated body 142 having a guidewire passage 144 extending at least through its distal portion (e.g., a rapid exchange, monorail style guidewire passage), and a balloon 146 disposed near a distal end of the elongated body 142.

A drug coating is positioned on the proximal balloon portion 146B so that it can impart a drug to a patient's vessel, while the distal balloon portion 146A is mostly or completely free of the drug coating. Hence, the distal balloon portion 146A can be expanded to occlude a vessel with little, if any, drug coating from this portion being dislodged and migrating distally of the catheter 140.

As seen in FIGS. 7-10, the balloon catheter 140 is configured such that it sequentially inflates and deflates the distal balloon portion 146A and the proximal balloon portion 146B. Specifically, the distal balloon portion 146A initially inflates, the proximal balloon portion 145B then inflates, the distal balloon portion 146A deflates, and then the proximal portion 145B deflates.

This sequential balloon inflation can be achieved by several different techniques. For example, each portion 146A, 146B of the balloon 146 can be composed of materials that allow the distal balloon portion 146A to inflate at lower pressure (i.e., easier to inflate) than the proximal balloon portion 146B. This difference in resistance to inflation between the two portions 146A, 146B can be achieved by composing the portions of different material, different material thicknesses, an extra layer/band of material over the proximal portion 146B, any combination of these techniques, or similar techniques. The elongated body 142 may also include a single inflation lumen in communication with the balloon 146 to allow for the inflation/deflation sequence. As with prior embodiments, the inflation mechanism can be a manually actuated device such a syringe or a motorized inflation device that can be programmed to achieve and hold specific, desired pressures necessary for the inflation sequence.

In another example, the balloon 146 may include a mechanism to deliver and withdraw the inflation media to the distal balloon portion 146A and the proximal balloon portion 146B at different rates to cause the sequential inflation. This can be achieved with a larger distal inflation port and a small proximal inflation port on the elongated body 142 underneath the balloon 146, a partial or full wall within the balloon separating the portions 146A, 146B, distal and proximal inflation ports with valves that open at different amounts, separate inflation lumens within the elongated body 142, or combinations of these features.

The balloon catheter 140 can be used in the following example procedure. First, a guidewire is advanced within a patient so that its distal end is located near a target area of the patient's vessel. Next, an elongated, tubular guide catheter 148 is advanced over the guidewire so that a distal end of the guide catheter 148 is positioned adjacent to the target area. Next, the balloon catheter 140 is advanced over the guidewire and through the internal lumen of the guide catheter 148 so that its distal end and balloon 146 are positioned at the target area of the patient's vessel. Preferably, the distal portion 146A is positioned distally of the target area while the drug coated proximal portion 146B is positioned circumferentially within the vessel's target area.

Referring to FIG. 7, the distal portion 146A of the balloon 146 is initially inflated so that it fully or substantially occludes the vessel. As seen in FIG. 8, the drug coated proximal portion 146B is inflated, causing its drug coated surface to expand against the target area of the vessel to impart or delivery some of its drugs.

Referring to FIG. 9, the proximal balloon portion 146B is partially or fully deflated, leaving any dislodged drug coating 143 within the blood trapped near the balloon 146. At this time, aspiration is applied via the guide catheter 148, though aspiration can also be applied prior to this point. This aspiration can be applied in a similar manner and with similar devices as described for previously described guide catheter 130.

Figure 10:
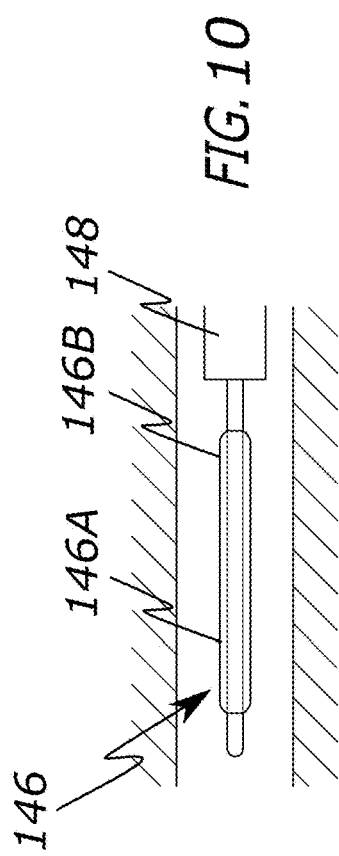
FIG. 10 is a side view of the sequentially inflatable balloon catheter of FIG. 5.

Finally, as seen in FIG. 10, the balloon 146 can be fully inflated and withdrawn back into the guide catheter 148 so that the procedure can be completed. The aspiration may optionally be continued during this full deflation and balloon withdrawal to further remove any drug coating that may become dislodged.

Figure 11:
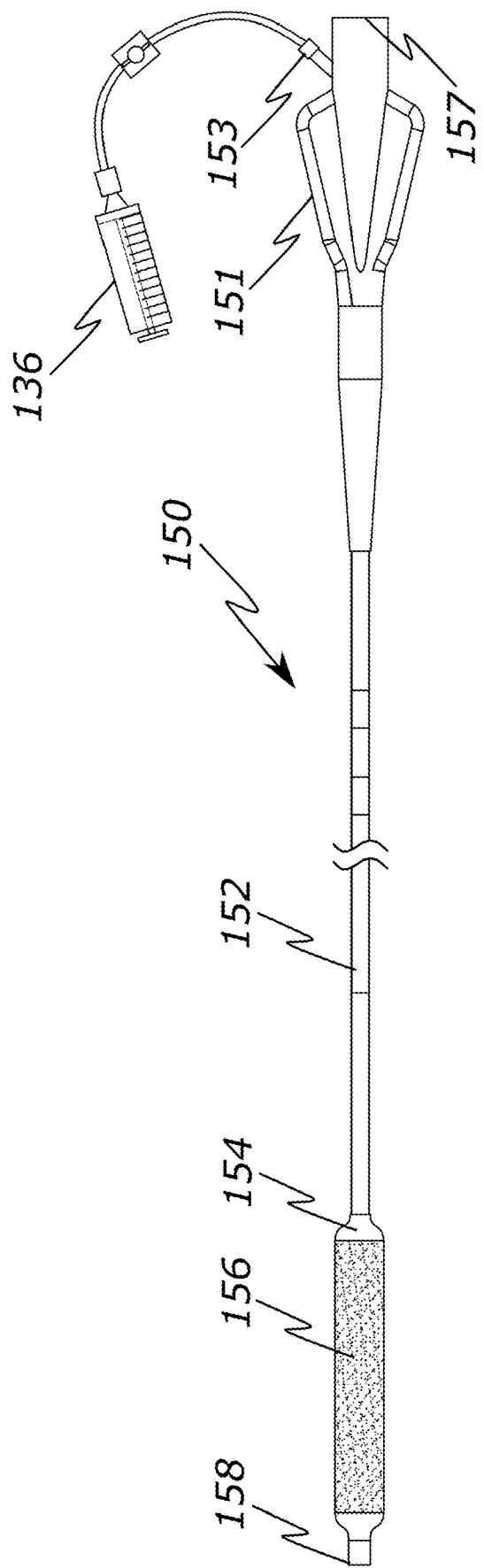
FIG. 11 is a side view of a balloon catheter with an enlarged guidewire passage.
Figure 12:
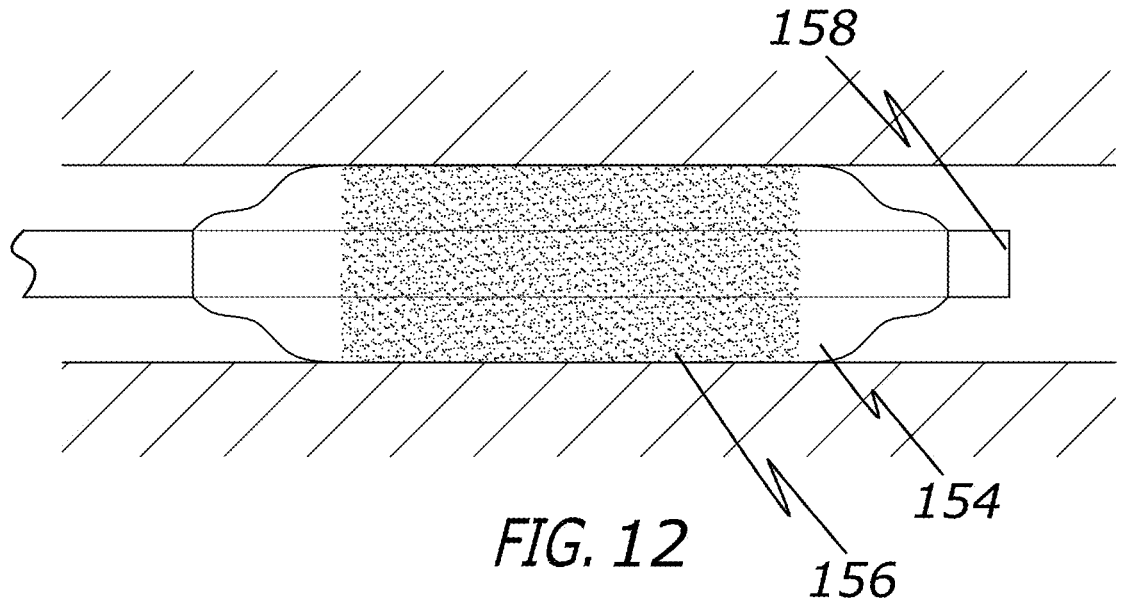
FIG. 12 is a side view of the balloon catheter of FIG. 11.
Figure 13:
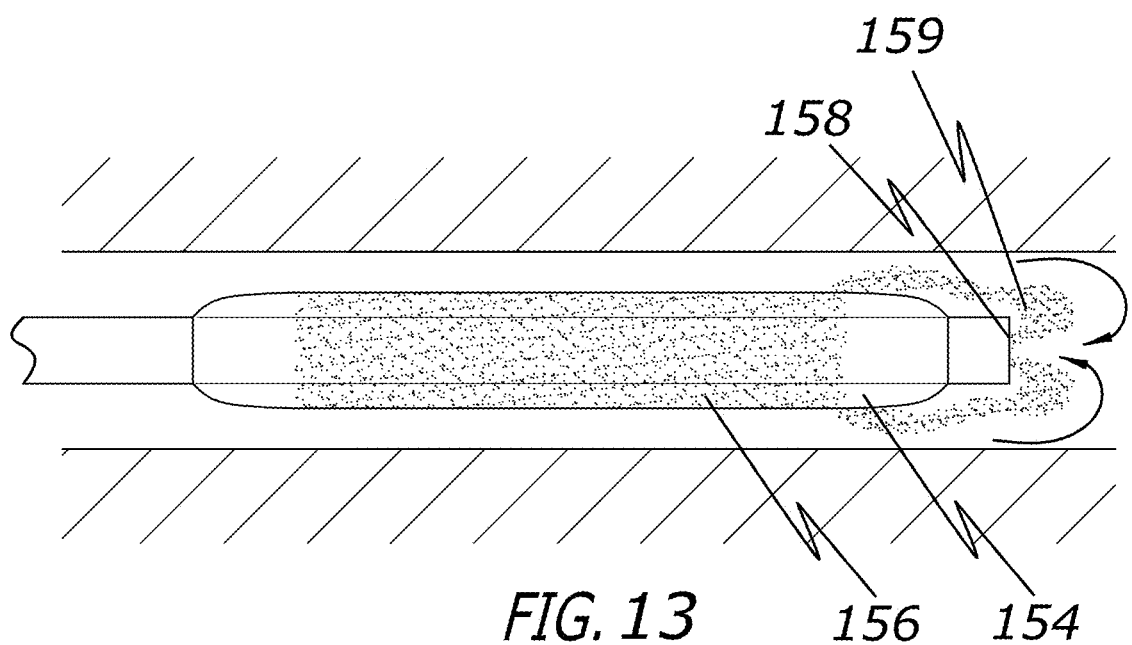
FIG. 13 is a side view of the balloon catheter of FIG. 11.

FIGS. 11-13 illustrate another embodiment of a balloon catheter 150 that is configured to allow aspiration via its distal end to help remove portions of dislodged drug coating 156. This distal aspiration can be optionally used with aspiration from a proximal side of the balloon 154 from a guide catheter (such as previously described guide catheters 130 and 148).

The balloon catheter 150 may comprise an elongated body having a guidewire passage that extends through the body that is also configured to also act as an aspiration passage. The passage may have a proximal opening 157 in the catheter's hub 151 that allows the guide wire to enter the passage, as well as a distal opening 158 that allows the guidewire to exit the passage. The catheter hub 151 may have an aspiration port 153 that is also in communication with the guidewire passage and is connectable to a vacuum source, such as a syringe 136. A hemodynamic valve in a proximal portion of the guidewire passage seals off the proximal end of the passage, and therefore when vacuum pressure is applied to the guidewire passage, it causes aspiration or suction out the distal opening 158 of the balloon catheter 150.

Optionally, the guidewire passage has a diameter that is somewhat larger than typical guidewire passages in order to prevent clogging during aspiration and ensure that the aspiration can remove blood at a desired rate. In one example, the diameter ratio of the guidewire/aspiration passage to the inflated balloon 154 is in a range inclusive of about 0.2 to 0.8. Some example ratios and measurements of prior art guidewire lumens and larger guidewire passage sizes according to the present embodiment are shown below in Table 1. For example, a guidewire lumen having a 0.036 mm diameter size and a 2 mm balloon diameter size results in a 0.18 ratio, while a 1.22 mm balloon diameter and a 2 mm balloon diameter has a ratio of 0.61.

TABLE 1

| Balloon Diameter | Example Prior Art Drug-Coated Balloon Catheters | | Present Embodiment with enlarged Guidewire-Aspiriation Passage | |
| --- | --- | --- | --- | --- |
| | (0.46 mm) GW Lumen | (0.36 mm) GW Lumen | 4F (.048") (1.22 mm) | 5F (.058") (148 mm) |
| 2 mm | NA | 0.18 | 0.61 | 0.74 |
| 4 mm | 0.12 | 0.09 | 0.31 | 0.37 |
| 7 mm | 0.07 | NA | 0.17 | 0.21 |

The balloon catheter 150 can be used in the following example procedure. First, a guidewire is advanced within a patient so that its distal end is located near a target area of the patient's vessel. Next, an elongated, tubular guide catheter (similar to guide catheters 130 or 148) is advanced over the guidewire so that a distal end of the guide catheter is positioned adjacent to the target area. Next, the balloon catheter 150 is advanced over the guidewire and through the internal lumen of the guide catheter so that its distal end and balloon 154 are positioned at the target area of the patient's vessel.

Referring to FIG. 12, the balloon 154 is inflated so that its drug coating 156 is pressed against the tissue of the target area. While the balloon 154 is being advanced out of the guide catheter and inflated, aspiration from the guide catheter (as described for previous embodiments) and/or aspiration from the distal opening 158 of the guidewire lumen can be applied to help collect any free drug coating 156 dislodged during this time.

Referring to FIG. 13, the balloon 154 can be deflated after a desired amount of contact time with the target area. Since this deflation may result in further dislodging more drug coating (shown in the blood as element 159), further aspiration helps capture and vacuum up the drug particles and blood from a distal end of the catheter 150. The aspiration according to this embodiment may only be applied through the distal opening 158 or in combination with aspiration from the guide catheter at various times throughout the procedure.

When applying aspiration from both the distal opening 158 and the guide catheter, it may be desirable to apply different vacuum pressures from each source, depending on how power the intended suction should be. For example, it may be desirable to employ a lower, gentler vacuum pressure from the distal opening 158 to prevent the patient's vessel from collapsing, while a relatively stronger vacuum source from the guide catheter may resist vessel collapse due to the balloon catheter extending distally outward of the guide catheter's opening.

Figure 14:
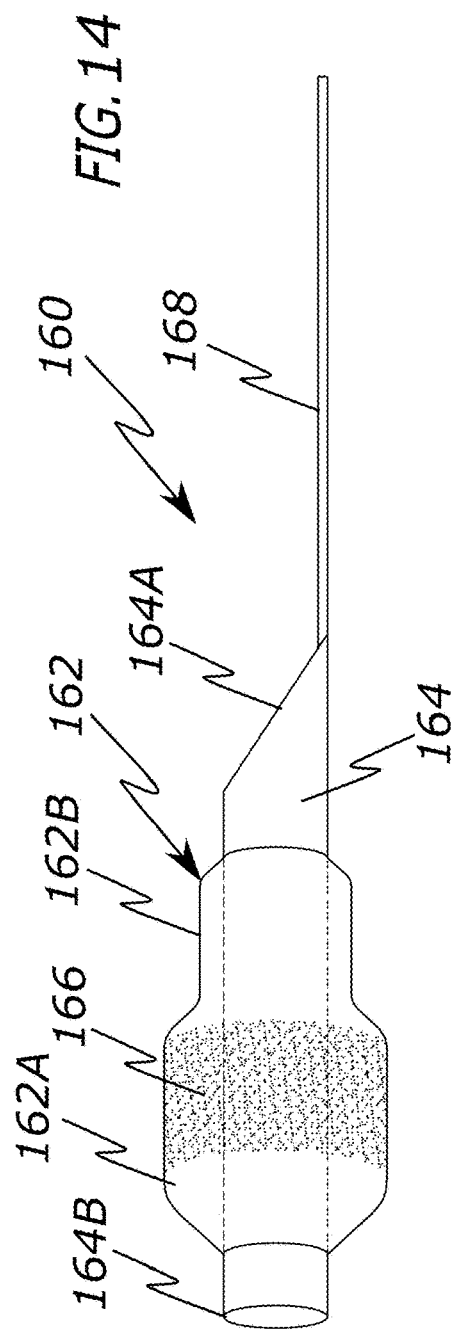
FIG. 14 is a side view of a balloon catheter.
Figure 15:
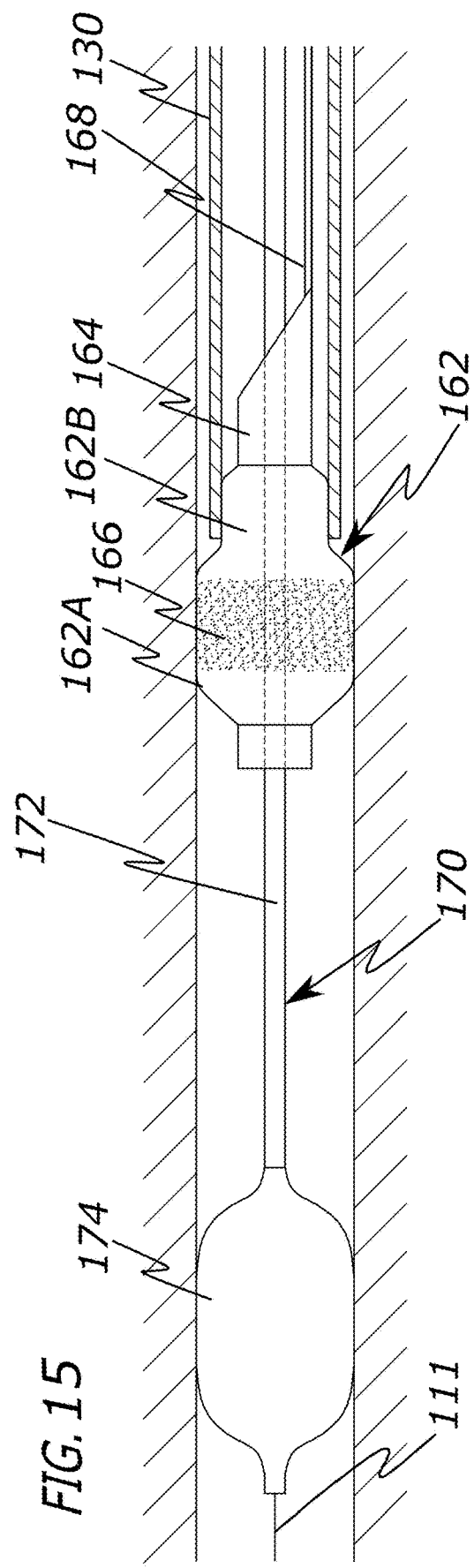
FIG. 15 is a side view of the balloon catheter of FIG. 14 with a guide catheter and an occlusion catheter.

FIGS. 14 and 15 illustrate another embodiment of a treatment system that allows selective aspiration proximally and distally of a drug coated balloon 162 during a procedure. Specifically, a drug-coated balloon catheter 160 is configured such that it can couple or sealingly engage with a distal opening of a guide catheter 130 connected to an aspiration source. This arrangement allows the guide catheter 130 to aspirate proximally of the balloon 162 when disconnected from the balloon 162, or distally of the balloon 162 through a passage 164 when engaged with a proximal end of the balloon 162, as seen in FIG. 15.

In one embodiment, the drug-coated balloon catheter 160 comprises an elongated catheter body 168 that is connected at its distal end to an enlarged tubular portion having a passage 164. The balloon 164 is connected on the enlarged tubular portion and configured to inflate via an inflation lumen within the elongated catheter body 168.

The balloon 162 is configured to inflate such that a distal balloon portion 162A has a larger inflated diameter and a proximal balloon portion 162B has a relatively smaller inflated diameter. The inflated diameter of the distal balloon portion 162A is preferably large enough to contact the inner diameter of a target vessel, allowing it to deliver some of its drug coating 166. The inflated diameter of the proximal balloon portion 162B has a diameter that is about the size of an inner diameter of the interior lumen of the guide catheter 130 (e.g., slightly greater than, equal to, or slightly smaller than the interior lumen). This sizing allows the inflated proximal balloon portion 162B to fit into and engage the inside of the guide catheter 130. Hence, when aspiration is applied to the guide catheter 130, it continues through the proximal opening 164A of the passage 164 and out the distal opening 164B. Alternately, the proximal balloon portion 1626 may inflate to a conical or ramped shape, increasing in the distal direction, so that it can "wedge" into the interior lumen of the guide catheter 130.

Optionally, the passage 164 has a diameter large enough to accommodate an occlusion balloon catheter 170 being passed through to allow an area of the vessel distal of the balloon 162 to be occluded, similar to previous embodiments. In one example, the passage 164 has a diameter to accommodate a 0.014" balloon, and therefore may have an inner diameter of about 0.050". In that regard, the passage 164 may have a diameter that provides a substantial amount of spacing around the body 172 of the balloon catheter 170 so that aspiration through the passage 164 can occur while the balloon catheter 170 is also located within the passage 164.

The balloon catheter 160 can be used in the following example procedure. First, a guidewire 111 is advanced within a patient so that its distal end is located near a target area of the patient's vessel. Next, an elongated, tubular guide catheter 130 is advanced over the guidewire 111 so that a distal end of the guide catheter 130 is positioned adjacent to the target area. Next, the drug-coated balloon catheter 160 is advanced over the guidewire (through passage 164) and through the internal lumen of the guide catheter 130 so that its distal end and balloon 162 are positioned at the target area of the patient's vessel.

Optionally, the occlusion balloon catheter 170 is advanced over the guide wire 111, and through the passage 164 of the drug-coated balloon catheter 160. The occlusion balloon 174 is then inflated to contact and occlude an area of the patient's vessel distal of the target area. This arrangement can be seen in FIG. 15.

Next, the balloon 162 of the drug-coated catheter 160 is inflated such that the drug coating 166 on its distal balloon portion 162A contacts the target area of the patient's vessel. During this time, the distal end of the guide catheter 130 may be positioned proximally apart from the balloon 162 and can apply aspiration in a manner previously discussed in other embodiments.

The distal end of the guide catheter 130 can then be moved distally toward the balloon 162 so that its lumen encompasses and overlaps the smaller-diameter portion 162B of the balloon 162. Aspiration through the guide catheter 130 is then activated, if it is not already active, creating suction in the space between the occlusion balloon 174 (if present) and the drug-coated balloon 162. Hence, any dislodged drug coating located in the blood between the two balloons 162, 174 is partially or completely removed.

Once a desired amount of aspiration has occurred, the drug-coated balloon 162 is deflated and withdrawn into the guide catheter 130. Similarly, the occlusion balloon 174 is deflated and withdrawn into the guide catheter 130, and the procedure can be completed.

In an alternate embodiment, any of the drug-coated balloons and/or occlusion balloons of the previously described embodiments can be replaced with non-inflatable devices such as expandable mesh devices.

In an alternate embodiment, the drug-coated balloons and balloon catheters of the previously described embodiments can be replaced with drug-coated stents (or similarly implantable devices) and stent delivery catheters.

In an alternate embodiment, the drug-coated balloons and balloon catheters of the previously described embodiments can be replaced with a balloon catheter having a balloon that "weeps" or slowly releases a liquid drug from pores in the surface of its balloon.

The procedures described in the present embodiments may be performed at many different locations within a patient's vascular system but may be particularly useful for procedures in the arms, legs, and torso.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vascular treatment system, comprising:
a guide catheter comprising an elongated tubular body and an aspiration port in fluid communication with an interior guide catheter lumen; and,
a drug-coated balloon catheter comprising a drug-coated balloon connected at a distal region of the drug-coated balloon catheter; wherein the drug-coated balloon has a distal portion on which a drug coating is disposed, and a proximal portion that has a fully inflated diameter sized to fit into and engage with the interior guide catheter lumen.

2. The vascular treatment system of claim 1, further comprising an enlarged tubular portion connected at the distal region of the drug-coated balloon catheter.

3. The vascular treatment system of claim 2, wherein the drug-coated balloon catheter has a first aspiration position, where in the first aspiration position the proximal portion of the drug-coated balloon is sealingly engaged with a distal opening of the interior guide catheter lumen, and where in the first aspiration position the enlarged tubular portion is in fluid communication with the interior guide catheter lumen and the aspiration.

4. The vascular treatment system of claim 3, wherein the drug-coated balloon catheter has a second aspiration position where in the second aspiration position the proximal portion of the drug-coated balloon is sealingly disengaged from the distal opening of the interior guide catheter lumen, and where in the second aspiration position the enlarged tubular portion is in fluid communication with the interior guide catheter lumen and the aspiration port.

5. The vascular treatment system of claim 4, wherein the drug-coated balloon is connected on the enlarged tubular portion.

6. The vascular treatment system of claim 1, wherein the distal portion of the drug-coated balloon has a fully inflated diameter that is larger than the fully inflated diameter of the proximal portion.

7. The vascular treatment system of claim 1, wherein the fully inflated diameter of the proximal portion of the drug-coated balloon is slightly greater than, equal to, or slightly smaller than the interior guide catheter lumen.

8. The vascular treatment system of claim 1, further comprising an occlusion balloon located distal to the drug-coated balloon.

9. The vascular treatment system of claim 2, further comprising an occlusion balloon catheter positioned through the enlarged tubular portion and having an occlusion balloon located distal to the drug-coated balloon.

10. A vascular treatment system, comprising:
a guide catheter comprising an elongated tubular body and an aspiration port in fluid communication with an interior guide catheter lumen; and,
a drug-coated balloon catheter comprising a drug-coated balloon connected at a distal region of the drug-coated balloon catheter, and an enlarged tubular portion connected at the distal region of the drug-coated catheter;
wherein the drug-coated balloon catheter has a first aspiration position where a proximal portion of the drug-coated balloon is sealingly engaged with a distal opening of the interior guide catheter lumen, and where the enlarged tubular portion is in fluid communication with the interior guide catheter lumen and the aspiration port; and,
wherein the drug-coated balloon catheter has a second aspiration position in which the proximal portion of the drug-coated balloon is sealingly disengaged from the distal opening of the interior guide catheter lumen, and where the enlarged tubular portion is in fluid communication with the interior guide catheter lumen and the aspiration port.

11. The vascular treatment system of claim 10, wherein the drug-coated balloon has a distal portion on which a drug coating is disposed, and a proximal portion that has an inflated diameter sized to fit into and engage with the interior guide catheter lumen.

12. The vascular treatment system of claim 10, wherein the drug-coated balloon is connected on the enlarged tubular portion.

13. The vascular treatment system of claim 10, wherein the distal portion of the drug-coated balloon has a fully inflated diameter that is larger than a fully inflated diameter of the proximal portion.

14. The vascular treatment system of claim 13, wherein the fully inflated diameter of the proximal portion of the drug-coated balloon is slightly greater than, equal to, or slightly smaller than the interior guide catheter lumen.

15. The vascular treatment system of claim 10, further comprising an occlusion balloon located distal to the drug-coated balloon.

16. The vascular treatment system of claim 10, further comprising an occlusion balloon catheter positioned through the enlarged tubular portion and having an occlusion balloon located distal to the drug-coated balloon.

17. The vascular treatment system of claim 16, wherein the enlarged tubular portion is about 0.050 inches.

18. The vascular treatment system of claim 10, wherein the drug-coated balloon has pores that release a liquid drug when the drug-coated balloon is inflated.

19. A vascular treatment system, comprising:
a guide catheter; and,
a drug-coated balloon catheter means for sealingly engaging a drug-coated balloon with a distal opening of an interior guide catheter lumen of the guide catheter in a first aspiration position, where in the first aspiration position the guide catheter is in fluid communication with a first space distal to the drug-coated balloon; and,
wherein the drug-coated balloon catheter further comprises means for sealingly disengaging from the distal opening of the interior guide catheter lumen in a second aspiration position, where in the second aspiration position the guide catheter is in fluid communication with a second space proximal to the drug coated balloon.

* * * * *